United States Patent [19]
Wong et al.

[11] Patent Number: 5,854,054
[45] Date of Patent: Dec. 29, 1998

[54] RATHAYIBACTER BIOPURESIS PRODUCES CEPHALOSPORIN HALOPEROXIDASE

[75] Inventors: Bing L. Wong, Durham, N.H.; Yong-Qiang Shen, Revere, Mass.; Yung-Pin Chen, Columbia, S.C.

[73] Assignee: Biopure Corporation, Cambridge, Mass.

[21] Appl. No.: 777,541

[22] Filed: Dec. 30, 1996

Related U.S. Application Data

[62] Division of Ser. No. 360,149, Dec. 20, 1994, Pat. No. 5,589,354.

[51] Int. Cl.$^6$ ........................................................ C12N 1/20
[52] U.S. Cl. ................................... 435/252.32; 435/842
[58] Field of Search ............................... 435/252.32, 843

[56] References Cited

U.S. PATENT DOCUMENTS

| | | | |
|---|---|---|---|
| 3,925,372 | 12/1975 | Chauvette | 540/215 |
| 4,064,343 | 12/1977 | Chauvette | 540/215 |
| 4,316,955 | 2/1982 | Abbott et al. | 435/47 |
| 4,672,114 | 6/1987 | von Daehne | 540/310 |
| 4,707,446 | 11/1987 | Hunter et al. | 435/132 |
| 4,707,447 | 11/1987 | Geigert et al. | 435/132 |

OTHER PUBLICATIONS

Zgurskaya et al. (1993) Internat. J. Syst. Bacteriol., 43(1), "*Rathayibacter* gen. nov., including the species *Rathayibacter rathayi* comb. nov., *Rathayibacter tritici* comb. nov., *Rathayibacter iranicus* comb. nov., and six strains from annual grasses", pp. 143–149.

Hayward (1993) Australasian Plant Pathology, 22 (4), "Phytopathogenic prokaryotes 1962–1992: An Australasian perspective ", pp. 113–121, Abstract in Biosis AN 94:231632.
Evtushenko et al., (1994) Russian Journal of Nematology, 2(2), "Coryneform bacteria from plant galls induced by nematodes of the subfamily *Anguininae*", pp. 99–104, Abstract in CABA, AN 95:100364.
Rainey et al. (1994) FEMS Microbiology Letters, 118 (1–2), "Further evidence for the phylogenetic coherence of actinomycetes with group B–peptidologlycan and evidence for the phylogenetic intermixing of the genera Microbacterium and Aureobacterium as determined by 16S rDNA analysis ", pp. 135–139.
Pickard et al. (1991). J. Indust. Microbiol., 7, "Chloroperoxidase, a Peroxidase with Potential ", pp. 235–242.
Franssen et al. (1992) Adv. Appl. Microbiol., 37, "Haolperoxidases: Their Properties and Their Use in Organic Synthesis ", pp. 41–98.
Neidleman (1975) CRC Crit. Rev. Biochem., 5, "Microbial Halogenation ", pp. 333–358.
van Péet al. (1985) J. Bacteriol., 161(3),"Purification of Bromoperoxidase from *Pseudomonas aureofaciens* ", pp. 1171–1175.

*Primary Examiner*—Jon P. Weber
*Attorney, Agent, or Firm*—Hamilton, Brook, Smith & Reynolds, P.C.

[57] ABSTRACT

An enzyme preparation that exhibits cephalosporin haloperoxidase activity is isolatable from a microorganism species of the *Rathayibacter* genus. This enzyme preparation can convert cephalexin to a halogenated cephalosporin antibiotic in a single step. A particular, unique microorganism that can provide the cephalosporin haloperoxidase enzyme preparation is *Rathayibacter biopuresis*.

6 Claims, 3 Drawing Sheets

*RATHAYIBACTER BIOPURESIS* PRODUCES CEPHALOSPORIN HALOPEROXIDASE

RELATED APPLICATION

This application is a division of application Ser. No. 08/360,149 filed Dec. 20, 1994, U.S. Pat. No. 5,589,354, which is incorporated herein by reference in its entirety.

BACKGROUND OF THE INVENTION

Cefaclor (7-[phenylglycylamido]-3-chloro-3-cephem-4-carboxylic acid) is an antibiotic of the cephalosporin class. Its antibiotic activity is effective against a range of bacteria including *Streptococcus pyogenes, Escherichia coli, Diplococcus pneumoniae, Shigella sp., Klebsiella pneumoniae, Aerobacter aerogenes* and *Salmonella heidelberg.* This antibiotic has been synthesized from parent compounds by synthetic organic techniques (see, e.g. U.S. Pat. Nos. 3,925,372 and 4,064,343). A common synthetic technique is to protect the 4-carboxylate by esterification, proceed by a series of steps to modify the 3 position so that a sole chloride atom is eventually covalently bound at that position, and then remove the ester protecting group from the carboxylate. In this manner a variety of cephalosporin antibiotics have been synthesized.

Another antibiotic in the cephalosporin family is cephalexin (7-[phenylglycylamido]-3-methyl-3-cephem-4-carboxylic acid). This antibiotic compound differs from cefaclor by the substitution of a methyl for the chloride at the 3 position. The synthesis of cephalexin is more easily achieved than the synthesis of cefaclor. However, the usefulness of cefaclor as an antibiotic surpasses that of cephalexin. For these reasons, it would be desirable to easily convert cephalexin to cefaclor. Synthetic organic routes can be utilized but, when these synthetic schemes are invoked, several steps are required to achieve this conversion. A simple, one-step process would be more desirable. Certain microorganisms contain haloperoxidases that can halogenate a wide variety of organic compounds (Franssen, M.C.R. et al., *Adv. Applied Microbiol.* 37: 41–99 (1992)). At the present time, these haloperoxidases do not appear to have commercial application as peroxidases. However, their use as halogenating agents has been sought. Despite optimistic predictions for the use of chloroperoxidases and other halogenating enzymes in the production of particular chemicals, the potential for the use of the haloperoxidases for this purpose remains unrealized. The major obstacles to fulfillment of these predictions lie in the narrow pH range of operation for these enzymes, the use of high concentrations of $H_2O_2$ which can be toxic to the source of the enzymes, and the short half-lives of the enzyme biocatalysts, to name a few.

Most haloperoxidases concomitantly convert a peroxide to water in the course of oxidizing the halide. Following this process, an enzymatic addition reaction occurs. However, to convert cephalexin to cefaclor, a substitution reaction is required; specifically, the substitution of a chloride for a methyl group. It would be desirable to have an enzyme preparation that not only halogenates an organic compound but also substitutes a halide such as a chloride for a methyl group on the organic compound at the same time. It would be especially desirable to have an enzyme that performs this substitution reaction at the appropriate position on a cephalexin molecule, thereby producing a halogenated product such as cefaclor.

SUMMARY OF THE INVENTION

This invention pertains to the production of antibiotics which are halogenated cephalosporins such as cefaclor. The production of this antibiotic occurs, in this invention, when a starting cephalosporin, cephalexin, is incubated under appropriate reaction conditions with an enzyme preparation termed cephalexin haloperoxidase. This enzyme preparation can be obtained from an appropriate microorganism. A particular microorganism of this invention which contains an enzyme preparation with cephalexin haloperoxidase activity is *Rathayibacter biopuresis* which is a unique strain of the *Rathayibacter* genus.

In the methods of the present invention, cephalexin is incubated with the cephalexin haloperoxidase enzyme preparation to allow the enzyme preparation (from the microorganism) to convert cephalexin into the halogenated product. The cephalexin haloperoxidase enzyme preparation in the methods of this invention is in the form of a crude extract from the microorganism.

BRIEF DESCRIPTION OF THE FIGURES

FIG. 1 is a photomicrograph of the *Rathayibacter biopuresis* microorganism.

FIG. 2 is a graphical representation of the protein content, eluant conductivity, and cephalexin chloroperoxidase activity as batches of substances are obtained from Toyo-Pearl Super Q anion-exchange resin that is loaded with the cell free crude extract from a *Rathayibacter biopuresis* homogenization procedure.

FIGS. 3A–3C are graphical representations of the separation of cephalexin and cefaclor by high pressure liquid chromatography (HPLC) techniques. FIG. 3A displays the output from a biocatalyst reaction solution; FIG. 3B displays a standard solution containing a known mixture of cephalexin and cefaclor; and FIG. 3C displays a combination of the biocatalyst reaction and mixed standard solutions.

DETAILED DESCRIPTION OF THE INVENTION

The present invention pertains to an enzymatic process for converting cephalexin to a halogenated product such as cefaclor.

In this process, a methyl group at the 3-position of cephalexin is replaced with a halogen. The halogen can be either iodine (I), bromine (Br), chlorine (Cl) or fluorine (F). In a preferred embodiment the halogen is Cl and the halogenated product is cefaclor. This enzymatic process eliminates several synthetic organic reaction steps that would otherwise be required to produce the halogenated product from a suitable starting material such as cephalexin. Since the enzymatic process is performed in an aqueous environment, traces of contaminating organic solvent do not remain with the halogenated product as it is recovered from the reaction mixture. Organic residues such as these traces of organic solvents often accompany products that are recovered after synthetic organic procedures. These organic residues can have unwanted and even deleterious effects if they are administered to humans with therapeutic products such as halogenated cephalosporin antibiotics. Thus, carrying out the total synthetic process in an aqueous environment is itself an improvement over a comparable synthetic organic procedure.

The enzymatic process of this invention converts cephalexin to the halogenated product in one step rather than in the several steps that would normally be required in a synthetic organic procedure. The halogenated product yield is enhanced by the use of a single step rather than several steps in a process to form this product from a particular starting material.

The enzymatic process of this invention is carried out by using constitutive enzymes of microorganisms which contain an enzyme preparation with the required specificity. The enzyme preparation from these microorganisms that display this specificity of converting cephalexin to a halogenated product such as cefaclor is termed cephalexin haloperoxidase. The enzyme preparation concomitantly uses a peroxide in the desired reaction of removing the methyl group from cephalexin and replacing it with a halogen radical.

The cephalexin haloperoxidase enzyme preparation of this invention comprises one or more enzymes which function independently or in combination to convert cephalexin to the halogenated product. The cephalexin haloperoxidase enzyme preparation can be characterized as being the fraction of substances that is eluted from a Toyo-Pearl Super Q anion-exchange resin in a 5 liter 0.3 M NaCl batch, in 50 mM phosphate buffer at pH 6.0, that follows a 5 liter 0.1 M NaCl (50 mM phosphate, pH 6.0) batch elution after the anion-exchange resin is loaded with the supernatant from a 15,000 xg (4° C.) centrifugation of a total homogenate of a Rathayibacter biopuresis culture.

The enzyme preparation, when used in the process of this invention, can be in a crude homogenate of or an extract from the host microorganisms. The enzyme preparation can be free in solution or immobilized on a solid support. In the latter configuration, the cephalexin is placed in an aqueous solution or mixture and this solution or mixture is allowed to flow past the immobilized enzyme preparation. The halogen product can then be recovered from the reaction system and further cephalexin introduced. In this or similar fashion, the halogenated product can be continually produced from cephalexin by reusing the enzyme preparation. If the enzyme preparation is not attached to a solid support but rather is free in solution, the halogenated product can be recovered by suitable means known to the skilled artisan, such as chromatographic or crystallization procedures.

The enzymatic process of this invention for producing a halogenated product from cephalexin is carried out under suitable conditions for the sought enzymatic conversion to be accomplished. The enzymatic reactions can be carried out in acid conditions with a pH between 3.5 and 7.0, preferably with a pH close to 5.5. A peroxide, preferably hydrogen peroxide, is present in the reaction solution or mixture. Potassium halide is also usually present in the reaction solution or mixture, preferably at a concentration of 50 mM. Sodium halide can alternatively be substituted for potassium halide in the reaction solution or mixture. When the halogenated product is cefaclor, the salt that is present is either potassium chloride or sodium chloride. The enzymatic reactions can be carried out in the presence of the following reaction constituents.

TABLE 1

| Constituent | Range | Preferred Value |
|---|---|---|
| 1. Buffer | | 100 mM |
| a. Acetate | pH 3.5–5.5 | pH 5.5 |
| b. Phosphate | pH 5.5–7.0 | pH 5.5 |
| 2. K halide or Na halide | 10–100 mM | 50 mM |
| 3. $H_2O_2$ | 2–50 mM | 10 mM |
| 4. Cephalexin | 0.1–100 mM | 1.5 mM |

The microorganisms of the present invention are those microbes that contain an isolatable enzyme preparation with cephalexin haloperoxidase activity. These microorganisms produce the halogenated product when they are incubated with cephalexin. Preferred microorganisms are bacteria from the *Rathayibacter* genus. These microorganisms are gram positive, aerobic and with coryneform morphology. A particularly preferred microorganism is *Rathayibacter biopuresis.* The *Rathayibacter biopuresis* microorganism is a heretofore unknown strain whose set of physiological properties (fatty acid and cell wall sugar constituency; saccharides, organic acids and amino acids utilization; production of acids; tolerance to salts; etc.) are distinctive. In particular, the amount of 16:0 cellular fatty acid in this microorganism is not present in other species of the *Rathayibacter* genus.

The subject matter of this invention is exemplified by the following Examples. These exemplifications are not to be construed as limiting, in any way, the disclosed invention, and modifications can be made within the abilities of the skilled artisan.

EXAMPLE 1

Isolation of Microorganism with Characteristic of Producing Cefaclor when Incubated with Cephalexin Microorganisms were obtained from the gut of the marine worm *Notomastus lobatus* and cultured. A specific microorganism of this group was isolated that contains an enzyme preparation that enzymatically converts cephalexin to cefaclor. An essentially pure culture of the isolated microorganism also yields an enzyme preparation that enzymatically converts cephalexin to cefaclor. The isolated microorganism is a bacterium of the *Rathayibacter* genus. The isolated bacterium was designated as *Rathayibacter biopuresis.* A culture of this isolated microorganism was deposited with the designation of RB 001 under conditions of the Budapest Treaty with the American Type Culture Collection (ATCC™), 12301 Parklawn Drive, Rockville, Md. 20852, USA on Dec. 1, 1996 under Accession Number ATCC 55728.

EXAMPLE 2

Taxonomic and Identifying Characteristics of the *Rathayibacter biopuresis* Microorganism In order to identify and taxonomically describe the isolated microorganism designated as *Rathayibacter biopuresis* of Example 1, the following media and testing procedures were used:

A. To determine the utilization of carbohydrates or organic acids as carbon sources. The isolated microorganisms were grown in a medium composed of:

| | |
|---|---|
| $(NH_4)_2SO_4$ | 0.1% |
| $KH_2PO_4$ | 0.15% |
| $K_2HPO_4$ | 0.15% |
| $MgSO_4.7H_2O$ | 0.05% |
| yeast extract | 0.01% |
| casamino acid | 0.01% |
| test carbohydrate or organic acid | 0.5% |
| at pH | 6.5 |

The negative control was the basal medium without a carbon source. The positive control was the basal medium supplemented with glucose. The procedures for determining the utilization of carbohydrates or of organic acids as carbon sources were essentially the same as those found in:

M.D. Collins et al., "Plant Pathogenic Species of Corynebacterium", p. 1276–1284, In P.H.A. Sneath et al. (ed.), *Bergey's Manual of Determinative Bacteriology*, The Williams & Wilkins Co., Baltimore (1986).

B. To determine whether acid was produced when the microorganisms were grown in the presence of particular carbon sources, the isolated microorganisms were grown in a medium composed of:

| | |
|---|---|
| $(NH_4)_2SO_4$ | 0.1% |
| $KH_2PO_4$ | 0.15% |
| $K_2HPO_4$ | 0.15% |
| $MgSO_4.7H_2O$ | 0.05% |
| yeast extract | 0.01% |
| casamino acid | 0.01% |
| Bromocresol purple | 0.0004% |
| test carbohydrate or organic acid | 0.5% |
| at pH | 7.0 |

A positive reaction occurred when there was a pronounced change of indicator color. The procedure for determining the production of acid when the microorganisms were grown in the presence of particular carbon sources was essentially the same as that found in the Collins et al. reference of Part A., above.

C. To determine the utilization of amino acids as sole nitrogen sources, the isolated microorganisms were grown in a medium composed of:

| | |
|---|---|
| glucose | 1% |
| NaCl | 0.05% |
| $K_2HPO_4$ | 0.1% |
| $MgSO_4.7H_2O$ | 0.05% |
| biotin | 10 mg/l |
| thiamine | 1 mg/l |
| test amino acid | 0.1% |
| at pH | 7.0 |

The procedure for determining the utilization of amino acids as sole nitrogen sources was essentially the same as that found in:

H. I. Zgurskaya et al., "*Rathayibacter* gen. nov., Including the Species *Rathayibacter rathayi* comb. nov., *Rathayibacter tritici* comb. nov., *Rathayibacter iranicus* comb. nov. and Six Strains from Annual Grasses", *Inter. J. Systemat. Bacteriol.* 43(1), 143–149 (1993).

D. To determine the tolerance of the microorganisms to NaCl or potassium tellurite, the isolated microorganisms were grown in a medium composed of:

| | |
|---|---|
| glucose | 1% |
| $K_2HPO_4$ | 0.15% |
| $KH_2PO_4$ | 0.15% |
| $MgSO_4.7H_2O$ | 0.05% |
| $(NH_4)_2SO_4$ | 0.1% |
| yeast extract | 0.01% |
| casamino acid | 0.01% | tested with 5% NaCl, 10% NaCl or 0.05% potassium tellurite

| | |
|---|---|
| at pH | 6.5 |

The procedure for determining the tolerance of the microorganisms to NaCl or potassium tellurite was essentially the same as that found in the Zgurskaya et al. reference of Part C., above.

E. To determine the ability of the microorganisms to hydrolyze Tweens 20, 40 or 85, the isolated microorganisms were grown in a medium composed of:

| | |
|---|---|
| $(NH_4)_2SO_4$ | 0.1% |
| $KH_2PO_4$ | 0.15% |
| $K_2HPO_4$ | 0.15% |
| $MgSO_4.7H_2O$ | 0.05% |
| yeast extract | 0.01% |
| casamino acid | 0.01% |
| test detergent | 0.5% |
| at pH | 6.5 |

The procedure for determining the ability of microorganisms to hydrolyze the Tweens was essentially the same as that found in the Zgurskaya et al. reference of Part C., above.

F. To determine whether the microorganisms can carry out the Voges-Proskauer reaction, the isolated microorganisms were grown in a medium composed of:

| | |
|---|---|
| glucose | 0.5% |
| $K_2HPO_4$ | 0.5% |
| bactopeptone | 0.5% |
| at pH | 7.0 |

The Voges-Proskauer reagent was prepared by dissolving 0.3 g creatine in 100 ml of 40% NaOH. After the microorganisms were incubated in the medium for 2–4 days, 3–5 ml of sample was taken and added to 1–2 ml of reagent solution. The mixture was shaken well. Positive results were indicated by the appearance of a pink color. Negative results were indicated by a yellow color. The procedure for determining whether the microorganisms can carry out the Voges-Proskauer reaction was essentially the same as that found in:

B. Davis et al., *Microbiology*, 4th Edition, p. 72, J. B. Lippincott Company (1990).

G. To determine whether the microorganisms can carry out a methyl red reaction, the isolated microorganisms were grown in the same medium as used for the Voges-Proskauer reaction. Methyl red was dissolved as 1 g in 250 ml of 60% alcohol. After the microorganisms were incubated in the medium for 4 days, a few drops of the methyl red reagent solution was added. A positive reaction was indicated by a red color. Negative results were indicated by unchanged color appearance. The procedure for determining whether the microorganisms can carry out a methyl red reaction was essentially the same as that found in the Collins et al. reference of Part A., above.

H. To determine the nitrate reduction, indole production, esculin hydrolysis, gelatin hydrolysis, urease, oxidase, arginine dihydrolase, β-galactosidase, pyrazinamidase, pyrrolidonyl arylamidase, alkaline phosphatase, β-glucuronidase, α-glucosidase and β-acetyl-β-glucosaminidase properties of the microorganisms, the appropriate reactions were performed using BioMerieux bacteria determination kits (BioMerieux Vitek, Inc., 595 Anglum Drive, Hazelwood, Mo. 63042) with the isolated microorganisms.

I. To determine whether the microorganisms have catalase activity, a drop of 3% $H_2O_2$ was added to an isolated microorganism culture. A positive reaction occurred when bubbles were formed. The procedure for determining whether the microorganisms have catalase activity was essentially the same as that found in the Collins et al. reference of Part A., above.

J. The fatty acid composition of the microorganisms was determined by routine gas chromatography techniques. Approximately 40 mg of *Rathayibacter biopuresis* microorganisms and 1 ml of saponification reagent (45 grams NaOH, 150 ml methanol and 150 ml distilled water) were placed in screw-top tubes. The tubes were securely sealed with Teflon lined caps and placed in a boiling water bath for 5 minutes. Each tube was then vigorously vortexed 6 times for 5–10 seconds each time. The tubes were cooled, uncapped and 2 ml of methylation reagent (325 ml of certified 6 N HCl and 275 ml of methyl alcohol) were added to each tube. The tubes were recapped and heated at 80° C. for 10 minutes. The tubes were again cooled and 1.25 ml of extraction reagent (200 ml of hexane and 200 ml of tert-butyl ether) were added to each tube. The tubes were gently tumbled on a clinical rotator for approximately 10 minutes. The tubes were uncapped and the aqueous phase withdrawn by pipette and discarded. Approximately 3 ml of washing reagent (10.8 grams of NaOH in 900 ml of distilled water) were added to the organic phase in each tube. The tubes were recapped and tumbled for 5 additional minutes. Approximately ⅔ of the organic phase from each tube was pipetted into a GC vial for subsequent analysis. The gas chromatographic procedures were performed on a 25 m×0.2 mm phenyl methyl silicone fused silica capillary column with a temperature program which increased the temperature from 170° C. to 270° C. at 5° C. per minute.

K. Morphological features of the microorganisms were determined by scanning electron microscopic techniques.

The following characteristics of the isolated microorganisms were observed:

1) Morphological characteristics (see FIG. 1)
   - a) Form and size: short rod with round end 369×1354 nm±31 nm
   - b) Motility: small population motile polar and monotrichous flagellum
   - c) Spore: no sporulation
   - d) Gram stain: positive
   - e) Fluorescent pigment: positive 2) Growth characteristics on particular media
   - a) Tryptic soy agar plate (28° C.)
     - i) Colony formation: 24 hours after inoculation
     - ii) Shape: regular circle with an entire edge
     - iii) Surface: smooth, low-convex, glossy
     - iv) Color: yellow
     - v) Smell: odoriferous, stale
   - b) Glycerol agar (28° C.)
     - i) Colony formation: 36 hours after inoculation
     - ii) Shape: regular circle with an entire edge
     - iii) Surface: smooth, low-convex, glossy
     - iv) Color: yellow
   - c) Glucose nutrient agar (28° C.)
     - i) Colony formation: 48 hours after inoculation
     - ii) Shape: regular circle with an entire edge
     - iii) Surface: smooth, low-convex, glossy
     - iv) Color: light yellow
   - d) Glucose nitrate agar (28° C.)
     - i) Colony formation: 48 hours after inoculation
     - ii) Shape: regular circle with an entire edge
     - iii) Surface: smooth, low-convex, glossy
     - iv) Color: light yellow 3) Physical properties

| | |
|---|---|
| a) nitrate reduction | + |
| b) methyl red test | + |
| c) Voges-Proskauer test | − |
| d) Indole formation | − |
| e) Gelatin hydrolysis | + |
| f) Starch hydrolysis | − |
| g) Esculin hydrolysis | + |
| h) Utilization of citrate | + |
| i) Catalase activity | + |
| j) Oxidase activity | + |
| k) Urease activity | − |
| l) Arginine dihydrolase activity | − |
| m) Alkaline phosphatase activity | − |
| n) β-galactosidase activity | + |
| o) β-glucuronidase activity | − |
| p) α-glucosidase activity | − |
| q) β-Acetyl-β-glucosaminidase activity | − |
| r) Pyrazinamidase activity | + |
| s) Pyrrolidonyl Arylamidase activity | − |
| t) Aerobic or anaerobic: | aerobic |
| u) Utilization of carbohydrates and organic acids: | |
| Xylose | + |
| Arabinose | + |
| Lactose | + |
| Mannitol | + |
| Sorbitol | + |
| Inulin | − |
| Glucose | + |
| Galactose | + |
| Fructose | + |
| Mannose | + |
| Maltose | + |
| Sucrose | + |
| Glycerol | + |
| Rhamnose | + |
| Melibiose | − |
| Tagatose | − |
| Citrate | + |
| Tartrate | − |
| Sebacinate | − |
| Malate | + |
| Glutarate | + | v) Acid production when grown with particular carbohydrates and organic acids:

| | |
|---|---|
| Xylose | − |
| Arabinose | + (weak) |
| Lactose | − |
| Mannitol | − |
| Sorbitol | − |
| Glucose | + |
| Galactose | + |
| Fructose | + |
| Mannose | + |
| Maltose | + |
| Sucrose | + |
| Glycerol | + |
| Rhamnose | + |
| Citrate | − |
| Malate | − |
| Glutarate | − | w) Tolerance to sodium chloride or potassium tellurite:

| | |
|---|---|
| 5% NaCl | − |
| 10% NaCl | − |
| 0.03% potassium tellurite | − | x) Hydrolysis of Tween 20, 40 and 85:

| | |
|---|---|
| Tween 20 (0.5%) | + |
| Tween 40 (0.5%) | + |
| Tween 85 (0.5%) | + | y) Amino acid utilization as nitrogen sources:

| | |
|---|---|
| Methionine | + |
| DL-valine | − |
| Glutamic acid | − |
| DL-Ornithine | + |

4) Cellular fatty acid composition as determined by gas chromatography:

| | | |
|---|---|---|
| iso | 14:0 | 0.67% |
| | 14:0 | 0.40% |
| iso | 15:0 | 4.33% |
| anteiso | 15:0 | 45.01% |
| | 15:0 | 0.23% |
| iso | 16:0 | 15.79% |
| | 16:0 | 11.64% |
| iso | 17:0 | 1.38% |
| anteiso | 17:0 | 20.34% |
| | 18:0 | 0.19% |

5) Comparison of differentiating characteristics of *Rathayibacter* species: The characteristics of the isolated microorganism were compared to the characteristics of other microorganisms in the *Rathayibacter* genus in Table 2.

TABLE 2

| Characteristic | R. rathayi* | R. tritici* | R. iranicus* | Rathayibacter sp.* | Rathayibacter biopuresis |
|---|---|---|---|---|---|
| Cell wall sugars | | | | | |
| Galactose | (+) | (+) | + | − | |
| Xylose | + | + | − | − | |
| Fatty acid composition (%) | | | | | |
| iso-15:0 | 1.8–4.7 | 0.0–4.3 | 0.9 | 0.0–2.3 | 4.33 |
| anteiso-15:0 | 39.2–73.5 | 28.7–45.6 | 42.1 | 32.7–46.8 | 45.01 |
| iso-16:0 | 7.6–15.7 | 15.5–36.1 | 21.1 | 10.2–20.4 | 15.79 |
| 16:0 | 0.0–2.7 | 3.0–5.2 | 3.3 | 0.9–1.8 | 11.64 |
| iso-17:0 | 0.0–3.5 | 0.0–0.0 | 1.1 | 0.4–1.7 | 1.38 |
| anteiso-17:0 | 10.0–33.8 | 18.4–38.0 | 28.0 | 39.8–16.7 | 20.34 |
| 17:0 | 0.0–0.07 | 0.0–2.5 | 0.4 | 0.9–3.3 | — |
| Utilization of: | | | | | |
| Xylose | + | + | − | + | |
| D-Arabinose | + | + | + | − | + |
| Lactose | + | + | + | − | + |
| Mannitol | + | + | + | − | + |
| Sorbitol | (+) | + | + | − | + |
| Inulin | − | + | − | — | + |
| Citrate | + | + | + | − | + |
| Tartrate | + | + | + | − | + |
| Sebacinate | (+) | + | − | − | − |
| Acid production from: | | | | | |
| Glucose | − | + | − | − | + |
| Galactose | − | (+) | + | − | + |
| Fructose | (+) | + | − | − | + |
| Mannose | − | + | + | − | + |
| Maltose | − | + | − | − | + |
| Xylose | + | + | + | − | − |
| Sucrose | − | + | − | − | + |
| Amino acid utilization | | | | | |
| DL-Valine | + | − | − | − | − |
| Glutamic acid | + | + | + | − | − |
| DL-Ornithine | + | + | + | − | − |

TABLE 2-continued

| Characteristic | R. rathayi* | R. tritici* | R. iranicus* | Rathayibacter sp.* | Rathayibacter biopuresis |
|---|---|---|---|---|---|
| Hydrolysis of Tween 21, Tween 40, and Tween 85 | + | + | + | − | − |
| Tolerance to: | | | | | |
| 5% NaCl | − | + | − | − | − |
| 0.030% potassium tellurite | (+) | + | + | − | − |
| Voges-Proskauer test | + | − | − | − | − |
| Methyl red test | + | + | − | − | + |
| susceptibility to iranicin | + | − | | + | N.D. |

*Zgurskaya, H.I. et al., J. Systematic Bacterioloqy 43(1): 143–149 (January, 1993)

The characteristics of the isolated microorganisms are differentiable from other species of the Rathayibacter genus by the following traits:

(1) The fatty acid composition profile of the isolated microorganism is unique. In particular, the percent of 16:0 cellular fatty acid is markedly higher than the percent of this fatty acid in other microorganisms of the genus.

(2) The carbohydrate utilization profile of the isolated microorganism is unique. In particular, the isolated microorganism utilizes inulin whereas *R. iranicus* does not. Likewise, although *R. Tritici* also utilizes inulin, *R. Tritici* utilizes sebacinate whereas the isolated microorganism (and *R. iranicus*) does not.

(3) The profile of acid production as a result of specific carbohydrate use for the isolated microorganism is unique. In particular, the isolated microorganism does not produce acid when xylose is metabolized whereas the other *Rathayibacter* species, with the exception of R. sp., do produce acid. On the other hand, R. sp. does not produce acid when several other carbohydrates (e.g. glucose, galactose, etc.) are metabolized whereas the isolated microorganism does produce acid as a result of metabolism of these carbohydrates.

(4) The amino acid utilization profile of the isolated microorganism is unique. In particular, the isolated microorganism does not utilize glutamic acid whereas the other *Rathayibacter* species, with the exception of R. sp., do utilize this amino acid. On the other hand, R. sp. does not utilize DL-ornithine whereas the isolated microorganism does utilize this amino acid.

On the bases of the high percentage of the 16:0 cellular fatty acid component (11.64%), the unique physiological properties (patterns of utilization of carbohydrates and of amino acids as well as acid production) for the *Rathayibacter biopuresis* microorganism, this microorganism was determined to be a unique strain of the *Rathayibacter* genus and, therefore, deserving of the *Rathayibacter biopuresis* designation.

EXAMPLE 3

Preparation of Cell Free Crude Extract Containing Cephalexin Chloroperoxidase from *Rathayibacter biopuresis*.

An inoculum of the isolated Rathayibacter biopuresis microorganism of Example 1 was placed in a seed medium composed of:

| | |
|---|---|
| $(NH_4)_2SO_4$ | 0.1% |
| NaCl | 0.25% |
| $KH_2PO_4$ | 0.15% |
| $K_2HPO_4$ | 0.15% |
| $MgSO_4.7H_2O$ | 0.05% |
| L-malic acid | 1.6% |
| Difco yeast extract | 0.2% |
| at pH | 6.10 before sterilization |

The inoculum size was 1–2%. Fermentation of the seed culture was performed at 28° C. for 20 hours in a 10 liter fermentor. The fermentation pH was maintained at pH 8.50 with 3 N HCl when the fermentation pH reached that level. Final fermentation of the culture was performed in the same medium as the seed medium above. This fermentation was performed at 28° C. for 25 hours in a 550 liter fermentor. Again the fermentation pH was maintained at pH 8.50 with 3 N HCl when the fermentation pH reached that level.

Approximately 1.3 kg (wet weight) of the *Rathayibacter biopuresis* microorganism from the fermentation broth produced in the 550 liter fermentor was collected by centrifugation and resuspended in 2600 ml of 50 mM phosphate buffer at pH 6.0 and then passed through a Cell 30 CD (AP Gaulin, Everett, Mass.) homogenizer twice at 14,000 psi. The temperature was controlled during this process to 4°–8° C. using an ice bath and a heat exchanger. The resulting ruptured cell mixture was then centrifuged (Sharples) at 15,000 xg (4° C.) for 15 minutes utilizing a batch mode. This centrifugation procedure was repeated once.

EXAMPLE 4

Conversion of Cephalexin to Cefaclor by Reaction with the Cephalexin Chloroperoxidase Preparation Cephalexin at a concentration of 10 mg/ml was incubated with the crude extract of the cephalexin chloroperoxidase preparation of Example 3 under a variety of reaction conditions and the amount of cefaclor produced was determined at identified reaction times by gas chromatographic (GC) techniques. Representative experimental conditions and results are shown below.

A. To assess the ability of the cephalexin chloroperoxidase reaction to be performed in an acidic environment, the enzymatic reaction was carried out under the following conditions:

| | |
|---|---|
| crude extract from Example 3 | 1 ml |
| KCl @ 0.5M | 100 μl |
| $H_2O_2$ @ 3% | 10 μl |
| cephalexin @ 10 mg/ml | 50 μl |
| pH was adjusted by adding 1N HCl to achieve the desired acidity. | |
| temperature | 37° C. |

The amounts of cefaclor produced at two pH values are shown in Table 3.

TABLE 3

| | Cefaclor Produced (μg/ml) | |
|---|---|---|
| Reaction Time (hours) | pH 5.9 | pH 2.85 |
| 12 | 0.42 | 0 |
| 44 | 3.8 | 2.4 |
| 65 | 5.5 | 2.5 |

B. To assess the utilization of $H_2O_2$ by the cephalexin chloroperoxidase preparation in the production of cefaclor, the enzymatic reaction was carried out under the following conditions:

| | |
|---|---|
| crude extract from Example 3 | 1 ml |
| KCl @ 0.5M | 100 μl |
| cephalexin @ 10 mg/ml | 50 μl |
| $H_2O_2$ was added at the designated concentrations in 10 μl of water. | |
| pH | 5.7 |

The amounts of cefaclor produced at various $H_2O_2$ concentrations and temperatures are shown in Table 4.

TABLE 4

| $H_2O_2$ Concentration | Reaction Time (hours) | Reaction Temp. (°C.) | Cefaclor Produced (μg/ml) |
|---|---|---|---|
| 0.3% | 33 | 37 | 0.4 |
| | 61 | 37 | 1.2 |
| 3.0% | 33 | 37 | 0.6 |
| | 61 | 37 | 2.8 |
| 30.0% | 18 | 42 | 3.9 |
| | 38 | 42 | 3.3 |

C. To assess the effects of KCl concentration on the production of cefaclor by the cephalexin chloroperoxidase preparation, the enzymatic reaction was carried out under the following conditions:

| | |
|---|---|
| crude extract from Example 3 | 0.8 ml |
| $KH_2PO_4$ @ 0.1M | 0.2 ml |
| $H_2O_2$ @ 3% | 10 μl |
| cephalexin @ 10 mg/ml | 50 μl |
| pH | 5.3 |
| temperature | 42° C. |

The amounts of cefaclor produced at various KCl concentrations are shown in Table 5.

TABLE 5

| KCl Concentration (mM) | Cefaclor Produced (μg/ml) |
|---|---|
| 25 | 7.0 |
| 50 | 9.2 |
| 75 | 5.1 |

The results of these assessments were that the enzyme functions in an acidic environment, utilizes $H_2O_2$, prefers KCl and a temperature of 37° C. or higher. The temperature can be at least 37°–42° C.

EXAMPLE 5

Partial Purification of Cephalexin Chloroperoxidase from *Rathayibacter biopuresis*.

The cell free crude extract of Example 3 was loaded onto an anion-exchange column which had been equilibrated with 50 mM phosphate buffer at pH 6.0 (Toyo-Pearl Super Q). DEAE-Sephadex A-50 or DE-52 anion-exchange resins can alternatively be used. The chloroperoxidase enzyme fraction was eluted from the column by using step gradients from 0 to 3.0 M of NaCl in 50 mM phosphate buffer at pH 6.0. Each step gradient batch was approximately 5 liters and the fractions collected were monitored by conductivity. When Super Q was used, the chloroperoxidase fraction eluted from the column at approximately 0.3 M NaCl with a conductivity range of 8–27 mS/cm. The protein amount, chloroperoxidase activity and conductivity for the fractions are displayed in FIG. 2. The batch containing peak enzyme activity was then concentrated by lyophilization using a Virtis lyophilizer.

EXAMPLE 6

Immobilization of the Cephalexin Chloroperoxidase Preparation from *Rathayibacter biopuresis.*

Twenty milligrams of the lyophilized protein from Example 5 was dissolved in 10 ml of 50 mM phosphate buffer at pH 5.5 together with 0.1 M NaCl. This solution was added to 1 gram of dry Eupergit C immobilization support. The solution slurry was gently shaken for 48–65 hours at room temperature. The residual protein solution was removed from the support material by filtration. The resultant immobilized biocatalyst was then washed 5 X with fresh 10 ml washes of distilled water. The washed immobilized biocatalyst was stored in 50 mM phosphate buffer at pH 5.5 together with 0.1 M NaCl at <10 degrees Celsius.

EXAMPLE 7

Conversion of Cephalexin to Cefaclor by Reaction with the Immobilized Cephalexin Chloroperoxidase Preparation.

The immobilized cephalexin chloroperoxidase preparation of Example 6 was used to enzymatically produce cefaclor from cephalexin under the following conditions:

| | |
|---|---|
| Immobilized biocatalyst from Example 6 | 5 gm (wet) |
| 0.1M Phosphate buffer, pH 6.0 | 10 ml |
| 3M NaCl | 9 μl |

| | |
|---|---|
| 10 mg/ml cephalexin | 486 μl |
| 3% H₂O₂ | 33 μl |

The reaction solution was incubated at 35 degrees Celsius with gentle shaking for 24 hours. The amount of cefaclor produced after 24 hours was assessed using ion pairing HPLC. The HPLC column was a Waters Novopak with a Novopak guard column. The mobile phase was 20% MeCN, 8 mM tetrabutylammonium hydroxide, pH 7.0. The column was at 30° C. and the mobile phase flow rate was 1.5 ml/min. The products were detected via a photodiode array detector over 195–300 nm with 258 nm as the specific detection wavelength. The yield of cefaclor from this immobilized biocatalytic process was 0.2% based on the starting quantity of cephalexin.

These results demonstrate that the immobilized enzyme can convert cephalexin to cefaclor. The preferred conditions for producing cefaclor using the immobilized enzyme are pH 6.0, 2.8 mM $H_2O_2$, 2.8 mM NaCl when 1.4 mM cephalexin starting material is present. The enzymatic reaction is carried out for 24 hours at 35 degrees Celsius.

Figure 1:
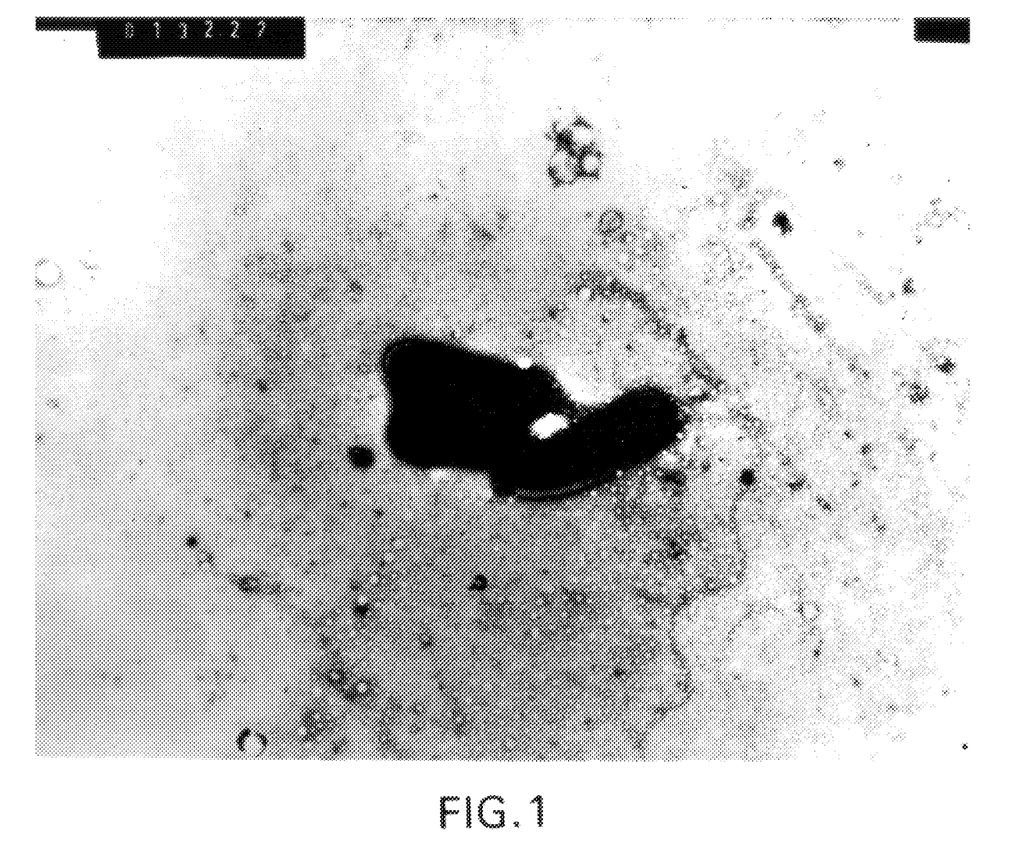
Figure 2:
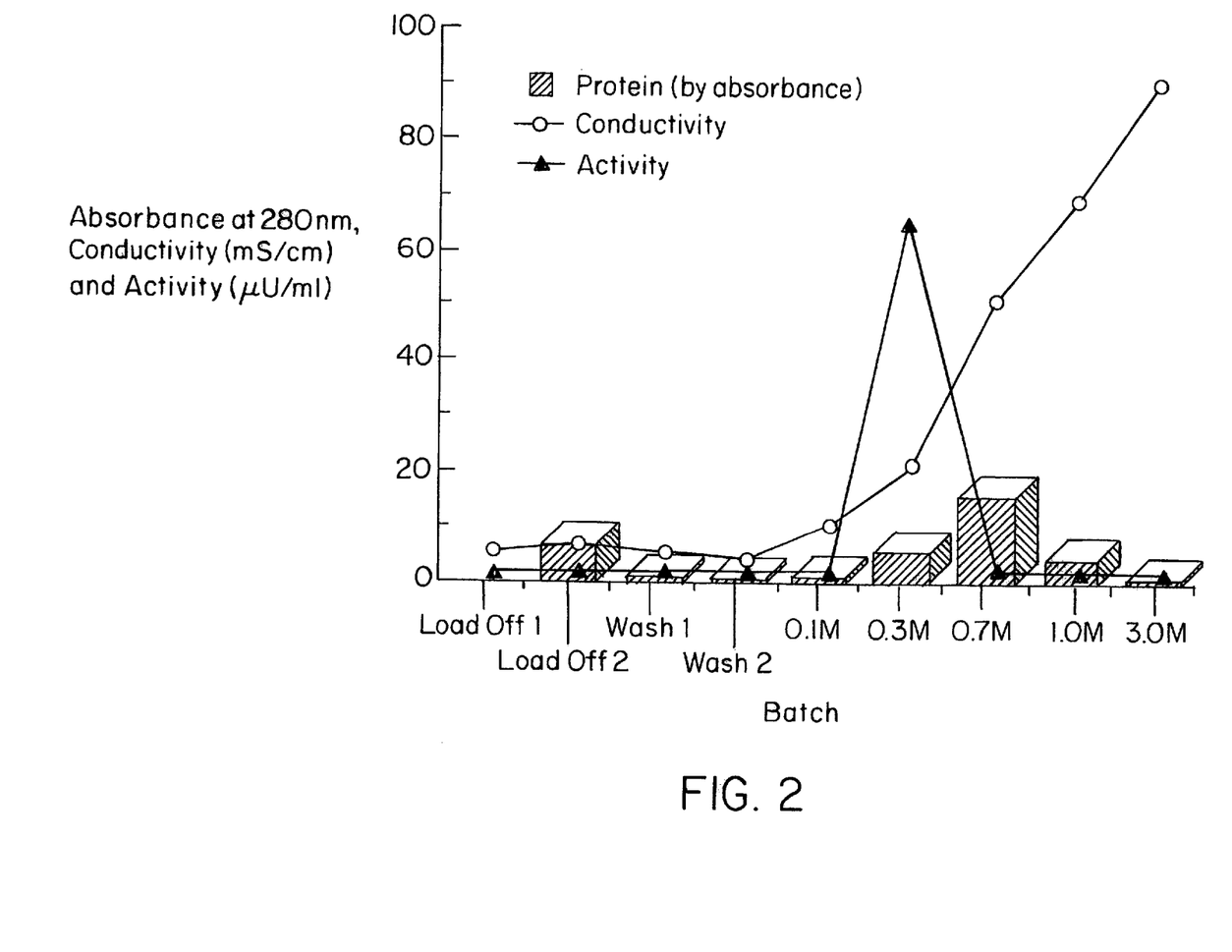
Figure 3A:
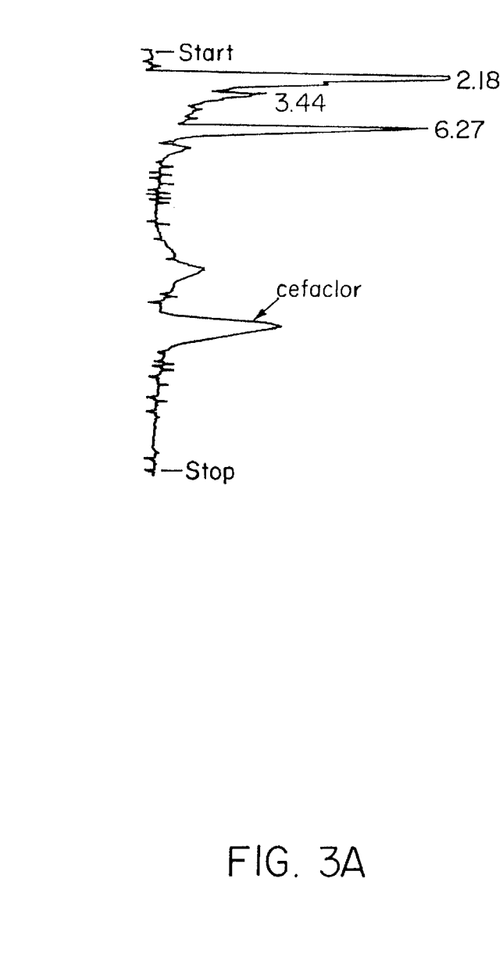
Figure 3B:
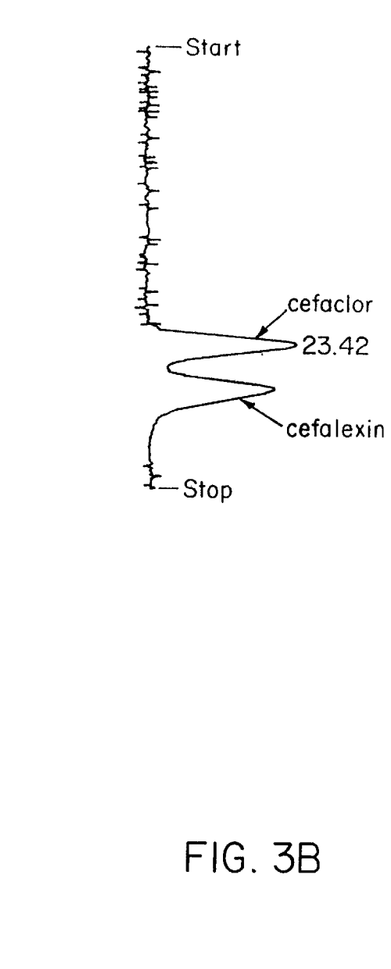
Figure 3C:
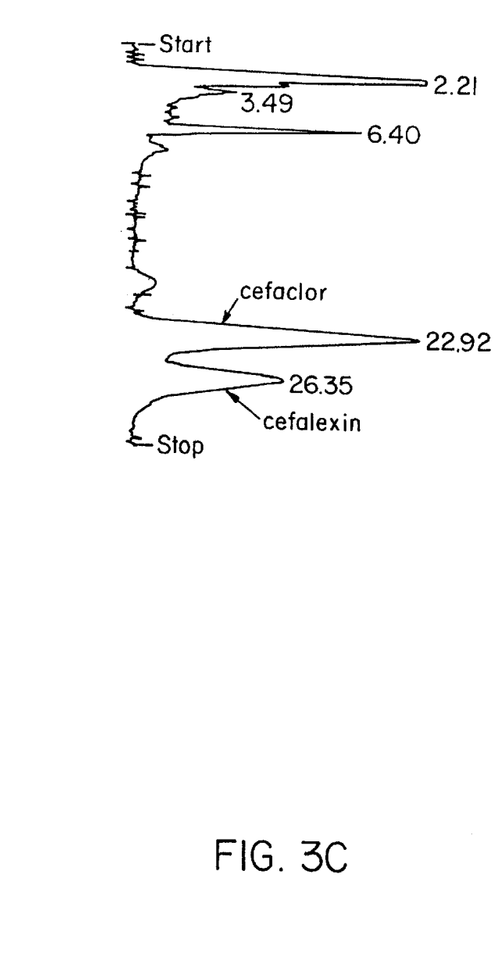

Another cephalexin to cefaclor reaction was performed where the cephalexin chloroperoxidase was not immobilized, i.e. the enzyme was free in solution. This reaction was allowed to continue for 24 hours. FIG. 3A is a graphical display of the HPLC separation of the biocatalyst reaction solution constituents following the 24 hour reaction period. FIGS. 3B and 3C are graphical displays of a mixed standard solution of cefaclor and cephalexin, and a mixture of the mixed standard solution and biocatalyst reaction output, respectively. The mixed standard contained equal amounts, by weight, of cefaclor and cephalexin in solution. These graphs demonstrate that cefaclor is produced by the cephalexin chloroperoxidase reaction with cephalexin and the cefaclor product can be easily identified in the reaction solution.

Equivalents

Those skilled in the art will recognize, or be able to ascertain using no more than routine experimentation, many equivalents to the specific embodiments of the invention described herein. Such equivalents are intended to be encompassed in the scope of the claims.

What is claimed is:

1. A biologically pure culture of a microorganism which produces an enzyme preparation with cephalosporin haloperoxidase activity which catalyzes the replacement reaction at the three position of the cephalosporin β-lactam ring system with a halogen.

2. The isolated microorganism of claim 1 comprising a species of the *Rathayibacter* genus.

3. The isolated microorganism of claim 2 comprising *Rathayibacter biopuresis*.

4. The isolated microorganism of claim 1 wherein the halogen of the haloperoxidase reaction is selected from the group consisting of iodine, bromine, chlorine and fluorine.

5. The isolated microorganism of claim 4 wherein the cephalosporin is cephalexin and the product of said cephalosporin haloperoxidase activity is cefaclor.

6. A biologically pure culture of a microorganism which produces an enzyme preparation with cephalexin haloperoxidase activity which catalyzes the replacement reaction at the three position of the cephalexin β-lactam ring system with halogen.

* * * * *